United States Patent
Kim et al.

(10) Patent No.: US 9,435,754 B2
(45) Date of Patent: Sep. 6, 2016

(54) FLAT PANEL TYPE X-RAY GENERATORS AND X-RAY IMAGING SYSTEMS INCLUDING THE SAME

(71) Applicant: Samsung Electronics Co., Ltd., Suwon-Si, Gyeonggi-Do (KR)

(72) Inventors: Il-Hwan Kim, Seoul (KR); Yong-Chul Kim, Seoul (KR); Shang-Hyeun Park, Yongin-si (KR); Tae-Won Jeong, Yongin-si (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 130 days.

(21) Appl. No.: 14/300,742

(22) Filed: Jun. 10, 2014

(65) Prior Publication Data
US 2015/0063540 A1 Mar. 5, 2015

(30) Foreign Application Priority Data
Aug. 27, 2013 (KR) .................. 10-2013-0102000

(51) Int. Cl.
*G01N 23/04* (2006.01)
*G21K 1/02* (2006.01)
*H01J 35/06* (2006.01)

(52) U.S. Cl.
CPC .............. *G01N 23/04* (2013.01); *G21K 1/025* (2013.01); *H01J 35/06* (2013.01); *G01N 2223/316* (2013.01); *H01J 2235/068* (2013.01)

(58) Field of Classification Search
CPC .......... G01N 23/04; H01J 35/14; G21K 1/25
USPC .................................................. 378/119–144
See application file for complete search history.

(56) References Cited

U.S. PATENT DOCUMENTS

| 6,229,870 | B1 * | 5/2001 | Morgan | A61B 6/032 378/4 |
| 6,975,703 | B2 | 12/2005 | Wilson et al. | |
| 2007/0024180 | A1 * | 2/2007 | Choi | B82Y 10/00 313/498 |
| 2012/0140895 | A1 | 6/2012 | Okunuki et al. | |

FOREIGN PATENT DOCUMENTS

| JP | 4599073 B2 | 12/2010 |
| KR | 100413946 B1 | 1/2004 |
| KR | 10-0680700 B1 | 2/2007 |

* cited by examiner

*Primary Examiner* — Courtney Thomas
(74) *Attorney, Agent, or Firm* — Harness, Dickey & Pierce, P.L.C.

(57) ABSTRACT

An X-ray generator may comprise: an electron emission device comprising a plurality of electron emission units configured to emit electrons; an X-ray emission device configured to emit X-rays due to the electrons emitted from the electron emission device; and/or a parallel light extraction member configured to extract X-rays having directivity from among the X-rays emitted from the X-ray emission device and to allow the extracted X-rays having directivity to pass through the parallel light extraction member.

19 Claims, 5 Drawing Sheets

FLAT PANEL TYPE X-RAY GENERATORS AND X-RAY IMAGING SYSTEMS INCLUDING THE SAME

CROSS-REFERENCE TO RELATED APPLICATION(S)

This application claims priority from Korean Patent Application No. 10-2013-0102000, filed on Aug. 27, 2013, in the Korean Intellectual Property Office (KIPO), the entire contents of which are incorporated herein by reference.

BACKGROUND

1. Field

Some example embodiments may relate to flat panel type X-ray generators. Some example embodiments may relate to X-ray imaging systems including flat panel type X-ray generators.

2. Description of Related Art

X-rays may be used in non-invasive testing, structural and physical properties testing, image diagnosis, security inspection, and the like in the fields of industry, science, medical treatment, etc. Generally, an imaging system using X-rays for such purposes may include an X-ray generator for radiating an X-ray and an X-ray detector for detecting an X-ray that has passed through an object.

The X-ray detector may be being rapidly converted from a filming method to a digital method, whereas the X-ray generator uses an X-ray source of a point light source type, that is, an electron generation device using a tungsten filament type cathode. Since the X-ray detector may be generally implemented in a flat panel type, which problematically may require a predetermined distance between the X-ray generator and the object in order to obtain an image from the X-ray source of the point light source type. Furthermore, the object may have a predetermined area and may need to be photographed by a single X-ray generator, which may make it impossible to select and photograph a specific part of the object. Accordingly, a flat panel type X-ray generator using an X-ray source of a surface light source type, which does not need to maintain a distance between the X-ray generator and an object and may select and photograph a specific part of the object, may be desired.

SUMMARY

Some example embodiments may provide flat panel type X-ray generators. Some example embodiments may provide X-ray imaging systems including flat panel type X-ray generators.

In some example embodiments, an X-ray generator may comprise: an electron emission device comprising a plurality of electron emission units configured to emit electrons; an X-ray emission device configured to emit X-rays due to the electrons emitted from the electron emission device; and/or a parallel light extraction member configured to extract X-rays having directivity from among the X-rays emitted from the X-ray emission device and to allow the extracted X-rays having directivity to pass through the parallel light extraction member.

In some example embodiments, the parallel light extraction member may comprise a plurality of through holes. The X-rays having directivity may only transmit through the plurality of through holes.

In some example embodiments, the plurality of through holes may be formed in a direction perpendicular to a surface of the X-ray emission device.

In some example embodiments, the parallel light extraction member may comprise material having no transmittance with respect to the X-rays.

In some example embodiments, the parallel light extraction member may comprise material having a mass attenuation coefficient greater than or equal to 50 $cm^2/g$ with respect to the X-rays.

In some example embodiments, the parallel light extraction member may comprise heavy metal or heavy metal oxide.

In some example embodiments, the parallel light extraction member may comprise lead (Pb), tungsten (W), molybdenum (Mo), or lead(II) oxide (PbO).

In some example embodiments, each of the plurality of through holes may have an aspect ratio greater than or equal to 30 and less than or equal to 900.

In some example embodiments, each of the plurality of through holes may have an aspect ratio greater than or equal to 200.

In some example embodiments, a thickness of the parallel light extraction member may be greater than or equal to 1 mm and less than or equal to 10 mm. A diameter of each of the plurality of through holes may be greater than or equal to 10 μm and less than or equal to 20 μm.

In some example embodiments, a distance between each of the plurality of through holes may be greater than or equal to 1 μm and less than or equal to 50 μm.

In some example embodiments, each of the plurality of through holes may be smaller in size than pixels in a corresponding X-ray detector.

In some example embodiments, each of the plurality of through holes may be filled with air.

In some example embodiments, the plurality of electron emission units may be configured two-dimensionally. The plurality of electron emission units may be driven independently from one another.

In some example embodiments, each of the plurality of electron emission units may comprise: a cathode electrode; an insulating layer on the cathode electrode and comprising a gate hole for exposing the cathode electrode; a gate electrode on the insulating layer; and/or an electron emission source on the cathode electrode and configured to be exposed through the gate hole.

In some example embodiments, the electron emission source may comprise a carbon nanotube (CNT), carbon nano-fiber, metal, silicon, oxide, diamond, diamond-like carbon (DLC), carbide compound, or nitrogen compound.

In some example embodiments, the X-ray emission device may comprise: an anode electrode configured to generate the X-rays due to the electrons emitted from the electron emission device; and/or an anode plate on the anode electrode configured to support the anode electrode.

In some example embodiments, the anode electrode may comprise metal comprising tungsten (W), molybdenum (Mo), silver (Ag), chromium (Cr), iron (Fe), cobalt (Co), copper (Cu), or metal alloy.

In some example embodiments, the anode plate may comprise material having a mass attenuation coefficient less than or equal to 1 $cm^2/g$ with respect to the X-rays.

In some example embodiments, the anode plate may comprise glass, quartz, or aluminum (Al).

In some example embodiments, the X-ray generator may further comprise: a sealing container configured to seal space between the electron emission device and the X-ray emission device.

In some example embodiments, an X-ray imaging system may comprise: an X-ray generator; and/or an X-ray detector separated from the X-ray generator so that an object may be provided between the X-ray generator and the X-ray detector. The X-ray generator may comprise: an electron emission device comprising a plurality of electron emission units configured two-dimensionally and driven independently from one another to emit electrons; an X-ray emission device configured to emit X-rays due to the electrons emitted from the electron emission device; and/or a parallel light extraction member configured to extract X-rays having directivity from among the X-rays emitted from the X-ray emission device and to allow the extracted X-rays having directivity to pass through the parallel light extraction member.

In some example embodiments, the parallel light extraction member may comprise a plurality of through holes. The X-rays having directivity may only transmit through the plurality of through holes.

In some example embodiments, the plurality of through holes may be formed in a direction perpendicular to a surface of the X-ray emission device.

In some example embodiments, the parallel light extraction member may comprise material having a mass attenuation coefficient greater than or equal to 50 cm$^2$/g with respect to the X-rays.

In some example embodiments, the parallel light extraction member may comprise heavy metal or heavy metal oxide.

In some example embodiments, each of the plurality of through holes may have an aspect ratio greater than or equal to 30 and less than or equal to 900.

In some example embodiments, a thickness of the parallel light extraction member may be greater than or equal to 1 mm and less than or equal to 10 mm. A diameter of each of the plurality of through holes may be greater than or equal to 10 μm and less than or equal to 20 μm.

In some example embodiments, a distance between each of the plurality of through holes may be greater than or equal to 1 μm and less than or equal to 50 μm.

In some example embodiments, each of the plurality of through holes may be smaller in size than pixels in the X-ray detector.

In some example embodiments, each of the plurality of through holes may be filled with air.

In some example embodiments, each of the plurality of electron emission units may comprise: a cathode electrode; an insulating layer on the cathode electrode and comprising a gate hole for exposing the cathode electrode; a gate electrode on the insulating layer; and/or an electron emission source on the cathode electrode and configured to be exposed through the gate hole.

In some example embodiments, the X-ray emission device may comprise: an anode electrode configured to generate the X-rays due to the electrons emitted from the electron emission device; and/or an anode plate on the anode electrode, configured to support the anode electrode.

In some example embodiments, the anode plate may comprise material having transmittance with respect to the X-rays.

In some example embodiments, the anode plate may comprise glass, quartz, or aluminum (Al).

In some example embodiments, the X-ray imaging system may further comprise: a sealing container configured to seal space between the electron emission device and the X-ray emission device.

In some example embodiments, at least one of the plurality of electron emission units may be configured to be driven to emit the X-rays having the directivity from the X-ray generator. The X rays emitted from the X-ray generator may transmit through at least a partial region of the object and reach the X-ray detector.

In some example embodiments, an X-ray generator may comprise: a first device configured to emit electrons; a second device configured to receive the emitted electrons and to emit X-rays due to the received electrons; and/or a third device configured to allow X-rays having directivity from among the emitted X-rays to pass through the third device.

In some example embodiments, the third device may comprise a plurality of through holes. The X-rays having directivity may pass through the plurality of through holes.

In some example embodiments, the plurality of through holes may be formed in a direction perpendicular to a surface of the second device.

In some example embodiments, the third device may comprise material having a mass attenuation coefficient greater than or equal to 50 cm$^2$/g with respect to the X-rays.

In some example embodiments, the X-ray generator may further comprise: a fourth device configured to seal space between the first device and the second device.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature, their shapes are not intended to illustrate the actual shape of a region of a device, and their shapes are not intended to limit the scope of the example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

Figure 1:
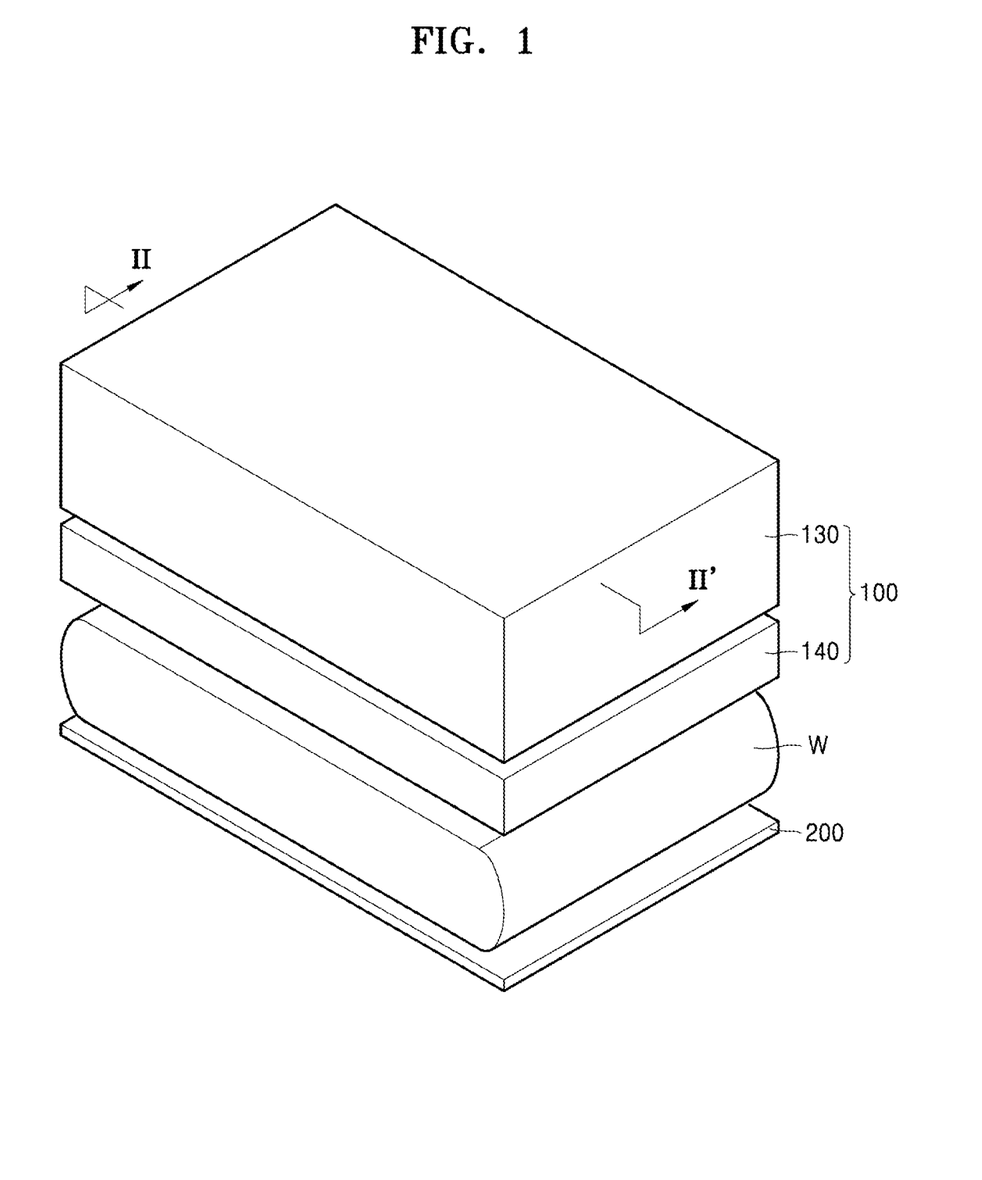
FIG. 1 is a perspective view of an X-ray imaging system according to some example embodiments.
Figure 2:
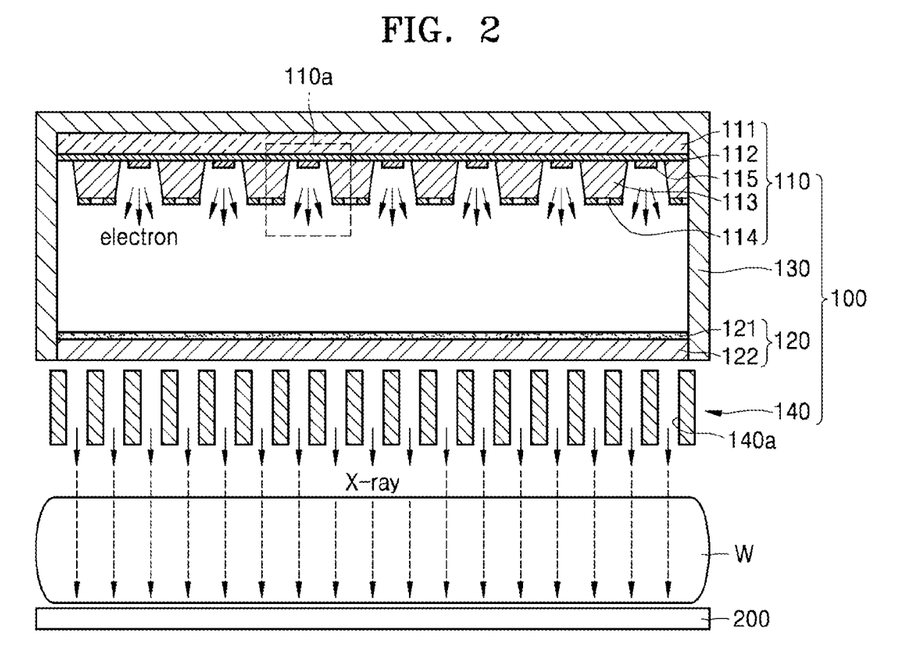
FIG. 2 is a cross-sectional view of the X-ray imaging system taken along line II-II' of FIG. 1.

FIG. 1 is a perspective view of an X-ray imaging system according to some example embodiments, and FIG. 2 is a cross-sectional view of the X-ray imaging system taken along line II-II' of FIG. 1.

In some example embodiments, by the term "X-ray", it is meant electromagnetic radiation having a wavelength greater than or equal to $10^{-11}$ m and less than or equal to $10^{-8}$ m.

Referring to FIGS. 1 and 2, the X-ray imaging system includes a flat panel type X-ray generator 100 and an X-ray detector 200 that detects an X-ray generated by the X-ray generator 100. An object W is disposed between the X-ray generator 100 and the X-ray detector 200. The X-ray detector 200 detects an X-ray that is emitted from the X-ray generator 100 and transmitted through the object W so that the inside of the object W may be photographed. In this regard, the object W may be provided such that the object W is in contact with the X-ray generator 100 and the X-ray detector 200. Alternatively, the object W may be provided such that the object W is in contact with the X-ray generator 100 or the X-ray detector 200. By disposing the object W between the flat panel type X-ray generator 100 and the X-ray detector 200, the X-ray imaging system may have a small thickness.

The flat panel type X-ray generator 100 includes an electron emission device 110 emitting electrons, an X-ray emission device 120 emitting X-rays by the electrons emitted from the electron emission device 110, and a parallel light extraction member 140 extracting an X-ray having directivity from the X-rays emitted from the X-ray emission device 120. In some example embodiments, the parallel light extraction member 140 may include or be embodied as, for example, a microchannel plate. In some example embodiments, the parallel light extraction member 140 may be interchangeable with other parallel light extraction members 140 (e.g., with different thicknesses 't' and/or different diameters 'D' of the through hole 140a).

In some example embodiments, the electron emission device 110 is an X-ray source of a surface light source type, and includes a plurality of electron emission units 110a that are two-dimensionally arranged. In some example embodiments, the electron emission units 110a are driven independently from one another to emit electrons selectively. The driving of two or more electron emission units 110a in a mutually linear relationship may provide improvements over an X-ray point source.

Figure 3:
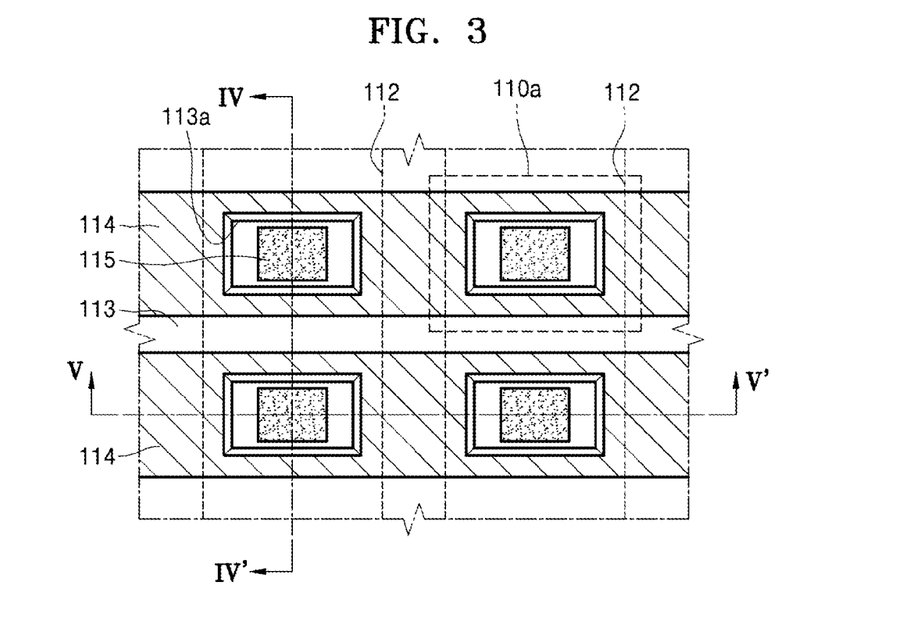
FIG. 3 is a plan view showing a part of an electron emission device of FIG. 1.
Figure 4:
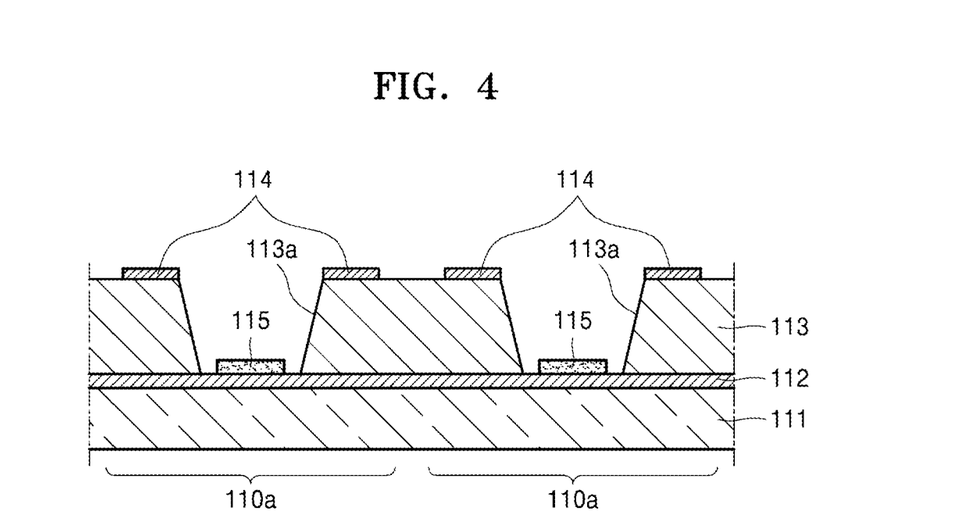
FIG. 4 is a cross-sectional view of the electron emission device taken along line IV-IV' of FIG. 3.
Figure 5:
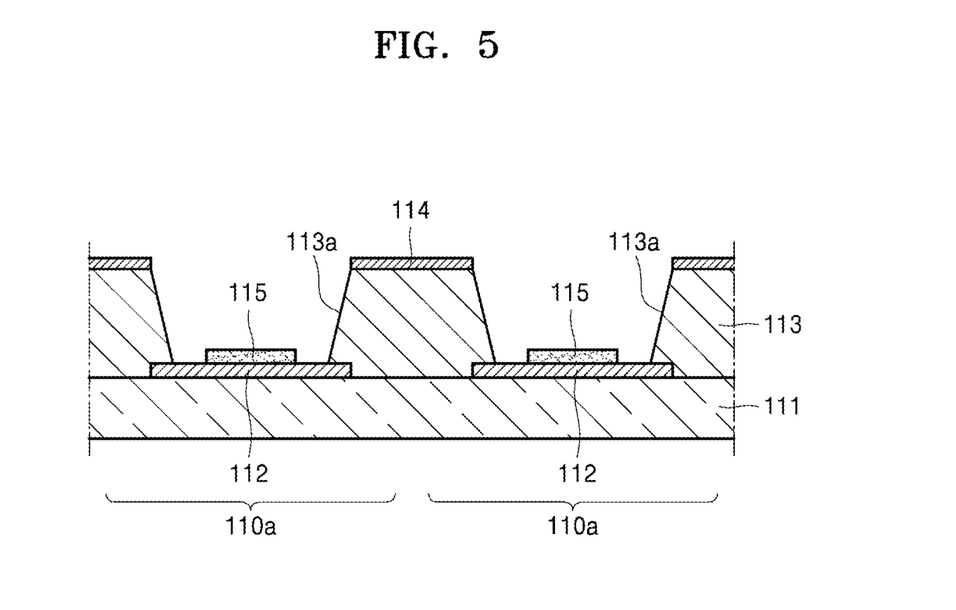
FIG. 5 is a cross-sectional view of the electron emission device taken along line V-V' of FIG. 3.

FIG. 3 is a plan view showing a part of the electron emission device 110 shown in FIG. 1. In addition, FIG. 4 is a cross-sectional view of the electron emission device 110 taken along line IV-IV' of FIG. 3, and FIG. 5 is a cross-sectional view of the electron emission device 110 taken along line V-V' of FIG. 3. Referring to FIGS. 3 through 5, a plurality of cathode electrodes 112 are formed on a substrate 111 in parallel with each other, and a plurality of gate electrodes 114 are formed on upper portions of the plurality of cathode electrodes 112 to cross the cathode electrodes 112. In addition, the electron emission units 110a are provided at points where the cathode electrodes 112 and the gate electrodes 114 cross each other. Such electron emission units 110a may be arranged on the substrate 111 in a two-dimensional matrix. In addition, each of the electron emission units 110a arranged in the two-dimensional way may operate independently from one another to emit electrons. That is, when predetermined voltages are applied respectively to one of the cathode electrodes 112 and one of the gate electrodes 114, the electron emission unit 110a provided at a point where the cathode electrode 112 and the gate electrode 114 to which the voltages are applied cross each other may be driven to emit electrons. Cathode electrodes 112 and gate electrodes 114 may drive electron emission units 110a in a manner similar to that in which row drivers and column drivers control a video display, so that no two electron emission units 110a are driven at the same time. Selective driving of specific electron emission units 110a may allow the driven electron emission units 110a to mimic a shape of the object to be imaged. Such mimicking may allow, for example, a reduced dose rate and/or reduced total dose for the object.

The electron emission unit 110a includes the cathode electrode 112, an insulating layer 113 disposed on the cathode electrode 112, the gate electrode 114 disposed on the insulating layer 113, and an electron emission source 115 emitting the electrons. The cathode electrode 112 is disposed on the substrate 111. The substrate 111 may be, for example, an insulating substrate such as a glass substrate; however, example embodiments are not limited thereto, that is, the substrate 111 may be a conductive substrate. In some example embodiments, an insulating layer (not shown) may be formed on a surface of the conductive substrate. The cathode electrode 112 may include a conductive material, for example, metal or a conductive metal oxide. In particular, the cathode electrode 112 may include metal such as titanium (Ti), platinum (Pt), ruthenium (Ru), gold (Au), silver (Ag), molybdenum (Mo), aluminum (Al), tungsten (W), and copper (Cu), or a metal oxide such as indium tine oxide (ITO), aluminum zinc oxide (AZO), indium zinc oxide (IZO), $SnO_2$, or $In_2O_3$. However, example embodiments are not limited thereto, that is, the cathode electrode 112 may include other various materials.

The insulating layer 113 is disposed on the cathode electrode 112, and the gate electrode 114 is disposed on the insulating layer 113. The insulating layer 113 insulates the cathode electrode 112 and the gate electrode 114 from each other. The insulating layer 113 may include, for example, $SiO_2$, $Si_3N_4$, $HfO_2$, or $Al_2O_3$; however, example embodiments are not limited thereto. A gate hole 113a exposing the cathode electrode 112 is formed in the insulating layer 113. In addition, the gate electrode 114 is disposed on the insulating layer 113. The gate electrode 114, like the cathode electrode 112, may include a conductive material. For example, the gate electrode 114 may include metal (e.g., aluminum (Al), chromium (Cr), copper (Cu), gold (Au), hafnium (Hf), molybdenum (Mo), nickel (Ni), palladium (Pd), platinum (Pt), silver (Ag), tantalum (Ta), titanium (Ti), tungsten (W), zirconium (Zr), or alloys thereof) or conductive metal oxide (e.g., indium tin oxide (ITO), indium zinc oxide (IZO), and the like).

The electron emission source 115 is disposed on the cathode electrode 112 that is exposed through the gate hole 113a. The electron emission source 115 emits electrons when a voltage is applied to the cathode electrode 112 and the gate electrode 114. The electron emission source 115 may include, for example, a carbon nanotube (CNT), carbon nano-fiber, metal, silicon, an oxide, a diamond, diamond-like carbon (DLC), a carbide compound, or a nitrogen compound. However, example embodiments are not limited thereto. The electron emission source 115 may be formed to have a height that is lower than that of the insulating layer 113. Although not shown in the drawings, a focusing electrode for focusing the electrons emitted from the electron emission source 115 may be further disposed on the gate electrode 114.

The X-ray emission device 120 includes an anode electrode 121 that generates the X-rays by the electrons emitted by the electron emission device 110, and an anode plate 122 disposed on the anode electrode 121. The anode electrode 121 may include, for example, metal such as tungsten (W), molybdenum (Mo), silver (Ag), chromium (Cr), iron (Fe), cobalt (Co), copper (Cu), etc., or a metal alloy. The anode electrode 121 may have relatively small thickness, for example, about 4 µm; however, example embodiments are not limited thereto. The anode electrode 121 may be manufactured integrally, or may be manufactured as being separated into a plurality of anode electrodes corresponding to the electron emission units 110a.

The anode plate 122 supports the anode electrode 121. The anode plate 122 may include a material through which the X-ray emitted from the anode electrode 121 may be transmitted. The anode plate may include, for example, a material having a mass attenuation coefficient less than or equal to 1 $cm^2/g$. The anode plate 122 may include, for example, glass, quartz, or aluminum (Al); however, example embodiments are not limited thereto. The anode plate 122 may be relatively thick so as to bear a variation in inner and outer pressures of a sealing container 130 that will be described later. For example, if the anode plate 122 is formed of aluminum (Al), the anode plate 122 may have a thickness of about 6 mm; however, example embodiments are not limited thereto.

The sealing container 130 for sealing a space between the electron emission device 110 and the X-ray emission device 120 is provided to surround the electron emission device 110 and the X-ray emission device 120. The sealing container 130 maintains the space between the electron emission device 110 and the X-ray emission device 120 in a vacuum state or to have a pressure close to the vacuum state, for example, about $10^{-6}$ Torr or less. The sealing container 130 may be formed of a material that is relatively strong enough to bear the variation in the inner and outer pressures of the sealing container 130.

The parallel light extraction member 140 is disposed under the X-ray emission device 120 to extract and emit the X-ray having directivity from the X-rays emitted from the X-ray emission device 120. In particular, the parallel light extraction member 140 extracts an X-ray having directivity from the X-rays emitted from the anode electrode 121 and transmitted through the anode plate 122, and emits the extracted X-ray toward the object W. For example, the parallel light extraction member 140 may extract the X-ray that is emitted nearly perpendicular to a surface of the anode plate 122.

Figure 6:
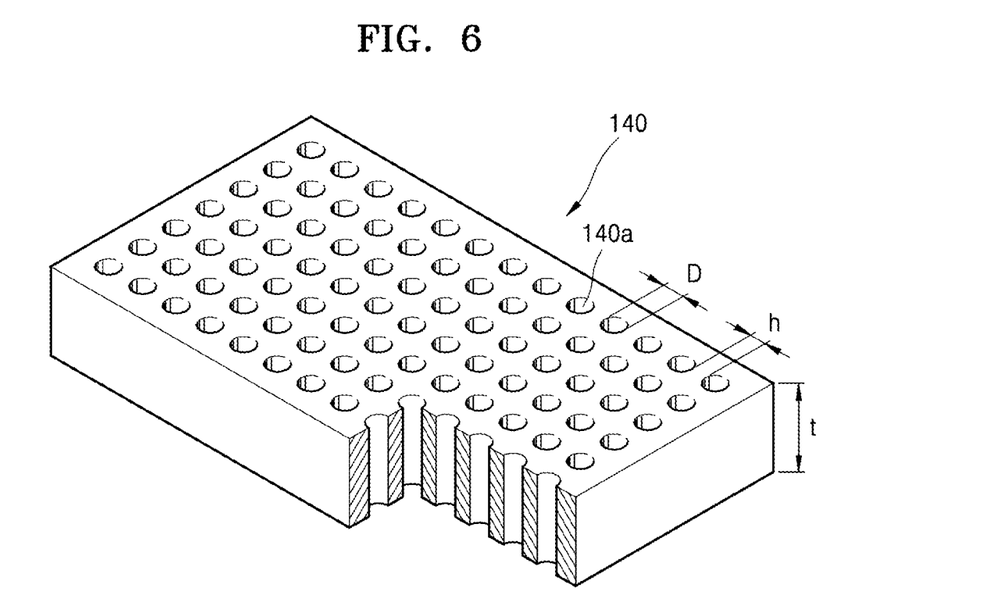
FIG. 6 is a perspective view of a parallel light extraction member shown in FIG. 1.
Figure 7:
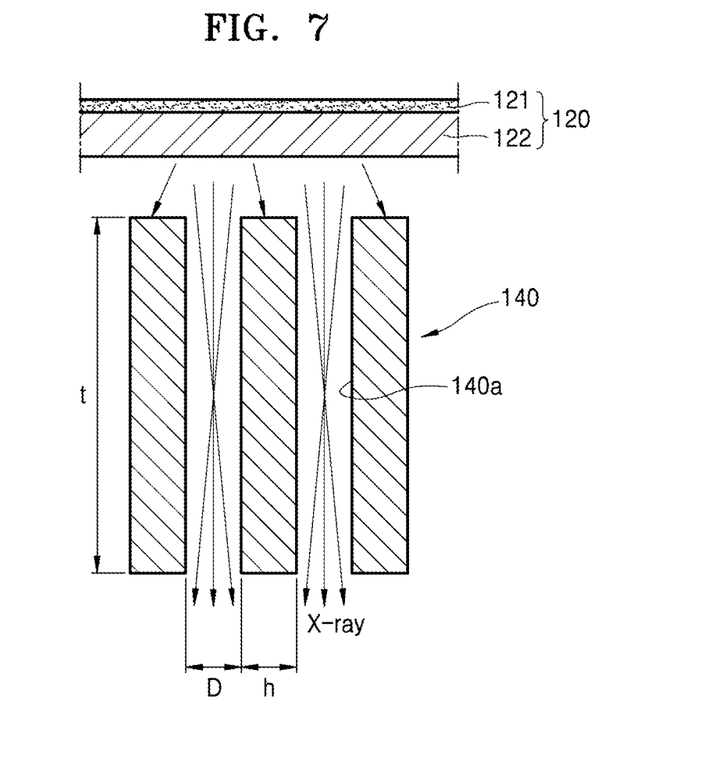
FIG. 7 is a cross-sectional view showing a part of the parallel light extraction member of FIG. 6.

FIG. 6 is a perspective view of the parallel light extraction member 140 shown in FIG. 1, and FIG. 7 is a cross-sectional view showing a part of the parallel light extraction member 140 of FIG. 6. Referring to FIGS. 6 and 7, the parallel light extraction member 140 includes a plurality of through holes 140a through which the X-ray having the directivity from among the X-rays emitted from the X-ray emission device 120 may only transmit. The through holes 140a of the parallel light extraction member 140 may correspond to the electron emission units 110a of the electron emission device 110 in a one-to-one correspondence. However, example embodiments are not limited thereto. That is, one through hole 140a may correspond to the plurality of electron emission units 110a, or a plurality of through holes 140a may correspond to one electron emission unit 110a. Such through holes 140a may be formed perpendicularly to the surface of the anode plate 122. The through holes 140a may be hollow, that is, the through holes 140a may be filled with air.

The parallel light extraction member 140 may include a material having no transmittance with respect to the X-ray, that is, a material absorbing the X-ray. In general, a physical property determining the transmittance of X-ray may be a mass attenuation coefficient. That is, a material having a large mass attenuation coefficient may absorb the X-ray well. Thus, the determination of whether the X-ray is absorbed is dependent upon the mass attenuation coefficient and a thickness of the material. For example, if the X-ray transmits through a lead(II) oxide (PbO) glass having a mass attenuation coefficient of 65.7 cm$^2$/g and a thickness of 25 μm, an intensity of the X-ray is reduced by half. In some example embodiments, the parallel light extraction member 140 may have a material that may absorb the X-ray sufficiently, that is, a material having a large mass attenuation coefficient. For example, the parallel light extraction member 140 may include a material having a mass attenuation coefficient greater than or equal to 50 cm$^2$/g; however, example embodiments are not limited thereto. In more detail, the parallel light extraction member 140 may include, for example, a heavy metal or a heavy metal oxide. The parallel light extraction member 140 may include lead (Pb), tungsten (W), molybdenum (Mo), PbO, or the like; however, example embodiments are not limited thereto, that is, the parallel light extraction member 140 may include other various materials. For example, the parallel light extraction member 140 may include water (e.g., demineralized water).

Referring to FIG. 7, from among the X-rays generated from the anode electrode 121 and transmitted through the anode plate 122, an X-ray emitted within a certain angle range with respect to the surface of the anode plate 122 (for example, an X-ray emitted nearly perpendicularly to the surface of the anode plate 122) pass through the through holes 140a formed in the parallel light extraction member 140. In addition, the X-ray outside of the certain angle range with respect to the surface of the anode plate 122 is incident to an upper surface of the parallel light extraction member 140, and the incident X-ray is absorbed and distinguished by the parallel light extraction member 140. Also, X-rays that enter a through hole 140a, but at such an angle that they hit the interior wall of the through hole 140a rather than passing straight through, may be absorbed by parallel light extraction member 140. That is, only the X-ray that has been transmitted through the through holes 140a from among the X-rays incident to the parallel light extraction member 140 may be discharged from the parallel light extraction member 140. Therefore, the X-ray emitted from the parallel light extraction member 140 has a certain directivity. For example, the X-ray emitted from the parallel light extraction member 140 may proceed in a direction nearly perpendicular to the surface of the anode plate 122.

The directivity or uniformity of the X-ray emitted from the parallel light extraction member 140 may be adjusted by an aspect ratio of the through hole 140a in the parallel light extraction member 140 or a distance between the through holes 140a. In some example embodiments, the aspect ratio of the through hole 140a denotes a ratio of a height of the through hole 140a to a diameter D of the through hole 140a. The height of the through hole 140a corresponds to a thickness 't' of the parallel light extraction member 140. The aspect ratio of the through hole 140a may be determined by a distance between the parallel light extraction member 140 and the X-ray detector 200, and a pixel size of the X-ray detector 200. For example, if the distance between the parallel light extraction member 140 and the X-ray detector 200 is large or the pixel size of the X-ray detector 200 is small, the aspect ratio of the through hole 140a may be increased. In some example embodiments, the through hole 140a may have a relatively large aspect ratio, for example, about several tens to several hundreds (e.g., greater than or equal to 30 and less than or equal to 900). For example, the through hole 140a may have an aspect ratio greater than or equal to 200; however, example embodiments are not limited thereto.

The height of the through hole 140a, that is, the thickness 't' of the parallel light extraction member 140 may be about a few mm to tens of mm (e.g., greater than or equal to 2 mm and less than or equal to 50 mm). In particular, the height of the through hole 140a may be about 1 mm to about 10 mm (e.g., greater than or equal to 1 mm and less than or equal to 10 mm); however, example embodiments are not limited thereto. In addition, the through hole 140a may have a size that is less than the pixel size of the X-ray detector 200 that will be described later; however, example embodiments are not limited thereto. In particular, the diameter 'D' of the through hole 140a may be about 10 μm to about 20 μm (e.g., e.g., greater than or equal to 10 μm and less than or equal to 20 μm); however, example embodiments are not limited thereto. A distance 'h' between the through holes 140a formed in the parallel light extraction member 140 may be several μm, for example, about 1 μm to about 50 μm (e.g., greater than or equal to 1 μm and less than or equal to 50 μm); however, example embodiments are not limited thereto. In addition, in the above description, a cross-section of the through hole 140a has a circular shape as an example; however, the through hole 140a may have a cross-section of various shapes.

The X-ray detector 200 is disposed to be separated from the parallel light extraction member 140 of the X-ray generator 100, and the object W, of which an X-ray image is to be obtained, is disposed between the parallel light extraction member 140 and the X-ray detector 200. In some example embodiments, the X-ray detector 200 may include a plurality of pixels (not shown) that are arranged two-dimensionally and are independently driven from one other. In some example embodiments, the pixels of the X-ray detector 200 may correspond to the electron emission units 110a of the X-ray generator 100 in one-to-one correspondence. Otherwise, each of the electron emission units 110a may correspond to two or more pixels, or each of the pixels may correspond to two or more electron emission units 110a. In some example embodiments, the ratio between the number of pixels and the number of the electron emission units 110a may be any ratio of whole numbers, such as 25:16, 12:42, etc.

In some example embodiments, the X-ray generator 100 may have a same area as the of the X-ray detector 200. In some example embodiments, the X-ray generator 100 may have a different area than the of the X-ray detector 200.

As described above, by providing the parallel light extraction member 140 under the X-ray emission device 120, only the X-ray having directivity may be irradiated to the object W. That is, of the X-rays emitted from the X-ray emission device 120, only the X-rays that pass through the parallel light extraction member 140 and then proceed nearly perpendicularly to the surface of the anode plate 122 may be emitted from the parallel light extraction member 140. In addition, the X-ray having the directivity transmits through the object W and, then, is detected by the X-ray detector 200. Accordingly, the X-ray detector 200 may obtain an X-ray image of high resolution.

Figure 8:
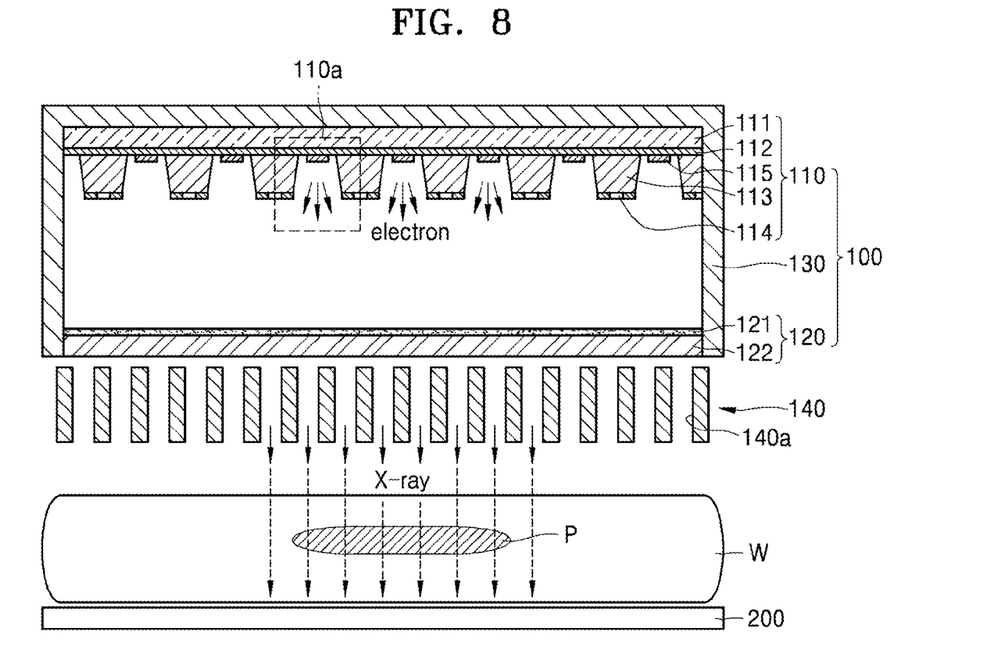
FIG. 8 is a cross-sectional view of an X-ray imaging system according to some example embodiments.

In some example embodiments, all the electron emission units 110a are driven as shown in FIG. 2 to irradiate the X-ray to entire area of the object W. However, only some of the electron emission units 110a may be driven to irradiate the X-ray to a partial area of the object W. FIG. 8 is a cross-sectional view of an X-ray imaging system according to some example embodiment. FIG. 8 shows an example embodiment in which some of the electron emission units 110a may be driven to irradiate the X-ray to a specific portion P of the object W. That is, referring to FIG. 8, only three electron emission units 110a are driven to emit electrons, and the X-ray is emitted from a part of the X-ray emission device 120 by the electrons emitted from the three electron emission units 110a. In addition, the X-ray emitted from the X-ray emission device 120 is changed to have a directivity while passing through the parallel light extraction member 140, and the X-ray having the directivity transmits through the specific portion P of the object W and reaches the X-ray detector 200. In some example embodiments, pixels of the X-ray detector 200 corresponding to the three electron emission units 110a are only driven to photograph the specific portion P of the object W.

According to the above X-ray imaging system, the parallel light extraction member in which the through holes 140a having large aspect ratios are formed is provided and, thus, only those X-rays having directivity may be irradiated to the object W. Accordingly, the X-ray image of high image quality and high resolution may be obtained. Also, since the X-ray imaging system includes the flat panel type X-ray generator of a surface light source type, the thickness thereof may be reduced.

It should be understood that example embodiments described herein should be considered in a descriptive sense only and not for purposes of limitation. Descriptions of features or aspects within example embodiments should typically be considered as available for other similar features or aspects in other example embodiments.

It should be understood that the example embodiments described herein should be considered in a descriptive sense only and not for purposes of limitation. Descriptions of features or aspects within each embodiment should typically be considered as available for other similar features or aspects in other embodiments.

What is claimed is:

1. An X-ray generator, comprising:
   an electron emission device comprising a plurality of electron emission units configured two-dimensionally to emit electrons;
   an X-ray emission device comprising a flat surface and emitting X-rays from the flat surface due to the electrons emitted from the electron emission device; and
   a parallel light extraction member configured to extract X-rays having directivity from among the X-rays emitted from the X-ray emission device and to allow the extracted X-rays having directivity to pass through the parallel light extraction member;
   wherein the parallel light extraction member comprises a plurality of through holes configured two-dimensionally, and
   wherein the plurality of through holes are formed in a direction perpendicular to the flat surface of the X-ray emission device.

2. The X-ray generator of claim 1,
   wherein the X-rays having directivity only transmit through the plurality of through holes.

3. The X-ray generator of claim 1, wherein the parallel light extraction member comprises material having no transmittance with respect to the X-rays.

4. The X-ray generator of claim 1, wherein the parallel light extraction member comprises material having a mass attenuation coefficient greater than or equal to 50 cm$^2$/g with respect to the X-rays.

5. The X-ray generator of claim 1,
   wherein the plurality of electron emission units are driven independently from one another.

6. The X-ray generator of claim 1, wherein each of the plurality of electron emission units comprises:
   a cathode electrode;
   an insulating layer on the cathode electrode and comprising a gate hole for exposing the cathode electrode;
   a gate electrode on the insulating layer; and
   an electron emission source on the cathode electrode and configured to be exposed through the gate hole.

7. The X-ray generator of claim 1, wherein the X-ray emission device comprises:
   an anode electrode configured to generate the X-rays due to the electrons emitted from the electron emission device; and
   an anode plate on the anode electrode configured to support the anode electrode.

8. The X-ray generator of claim 1, further comprising:
   a sealing container configured to seal space between the electron emission device and the X-ray emission device.

9. An X-ray imaging system, comprising:
   an X-ray generator; and
   an X-ray detector separated from the X-ray generator so that an object may be provided between the X-ray generator and the X-ray detector;
   wherein the X-ray generator comprises:
      an electron emission device comprising a plurality of electron emission units configured two-dimensionally and driven independently from one another to emit electrons;
      an X-ray emission device comprising a flat surface and emitting X-rays from the flat surface due to the electrons emitted from the electron emission device; and
      a parallel light extraction member configured to extract X-rays having directivity from among the X-rays emitted from the X-ray emission device and to allow the extracted X-rays having directivity to pass through the parallel light extraction member;
   wherein the parallel light extraction member comprises a plurality of through holes configured two-dimensionally, and
   wherein the plurality of through holes are formed in a direction perpendicular to the flat surface of the X-ray emission device.

10. The X-ray imaging system of claim 9,
    wherein the X-rays having directivity only transmit through the plurality of through holes.

11. The X-ray imaging system of claim 9, wherein the parallel light extraction member comprises material having a mass attenuation coefficient greater than or equal to 50 cm$^2$/g with respect to the X-rays.

12. The X-ray imaging system of claim 9, wherein each of the plurality of electron emission units comprises:
- a cathode electrode;
- an insulating layer on the cathode electrode and comprising a gate hole for exposing the cathode electrode;
- a gate electrode on the insulating layer; and
- an electron emission source on the cathode electrode and configured to be exposed through the gate hole.

13. The X-ray imaging system of claim 9, wherein the X-ray emission device comprises:
- an anode electrode configured to generate the X-rays due to the electrons emitted from the electron emission device; and
- an anode plate on the anode electrode, configured to support the anode electrode.

14. The X-ray imaging system of claim 9, further comprising:
- a sealing container configured to seal space between the electron emission device and the X-ray emission device.

15. The X-ray imaging system of claim 9, wherein at least one of the plurality of electron emission units is configured to be driven to emit the X-rays having the directivity from the X-ray generator, and
  wherein the X-rays emitted from the X-ray generator transmit through at least a partial region of the object and reach the X-ray detector.

16. An X-ray generator, comprising:
- a first device configured to emit electrons;
- a second device comprising a flat surface and emitting X-rays from the flat surface due to the electrons emitted from the first device; and
- a third device configured to allow X-rays having directivity from among the emitted X-rays to pass through the third device;
  wherein the third device comprises a plurality of through holes configured two-dimensionally, and
  wherein the plurality of through holes are formed in a direction perpendicular to the flat surface of the second device.

17. The X-ray generator of claim 16,
  wherein the X-rays having directivity pass through the plurality of through holes.

18. The X-ray generator of claim 16, wherein the third device comprises material having a mass attenuation coefficient greater than or equal to 50 $cm^2/g$ with respect to the X-rays.

19. The X-ray generator of claim 16, further comprising:
- a fourth device configured to seal space between the first device and the second device.

* * * * *